(12) United States Patent
Uddin

(10) Patent No.: US 9,301,935 B2
(45) Date of Patent: Apr. 5, 2016

(54) BROAD SPECTRUM PHARMACOLOGICAL COMPOSITION FOR TREATMENT OF VARIOUS INFECTIONS AND DISEASES AND METHODS OF USE

(71) Applicant: Naeem Uddin, Karachi (JP)

(72) Inventor: Naeem Uddin, Karachi (JP)

( * ) Notice: Subject to any disclaimer, the term of this patent is extended or adjusted under 35 U.S.C. 154(b) by 97 days.

(21) Appl. No.: 13/913,555

(22) Filed: Jun. 10, 2013

(65) Prior Publication Data

US 2014/0364504 A1 Dec. 11, 2014

(51) Int. Cl.

| | |
|---|---|
| *A61K 31/194* | (2006.01) |
| *A61K 31/56* | (2006.01) |
| *A61K 31/573* | (2006.01) |
| *A61K 31/60* | (2006.01) |
| *A61K 33/30* | (2006.01) |
| *A61K 47/00* | (2006.01) |
| *A61K 8/362* | (2006.01) |
| *A61K 8/365* | (2006.01) |
| *A61Q 3/00* | (2006.01) |
| *A61Q 5/00* | (2006.01) |
| *A61Q 5/02* | (2006.01) |
| *A61Q 7/00* | (2006.01) |
| *A61Q 19/00* | (2006.01) |
| *A61K 9/00* | (2006.01) |
| *A61K 9/02* | (2006.01) |
| *A61K 33/32* | (2006.01) |

(52) U.S. Cl.
CPC .............. *A61K 31/194* (2013.01); *A61K 8/362* (2013.01); *A61K 8/365* (2013.01); *A61K 9/0014* (2013.01); *A61K 9/0019* (2013.01); *A61K 9/0031* (2013.01); *A61K 9/02* (2013.01); *A61K 31/56* (2013.01); *A61K 31/573* (2013.01); *A61K 31/60* (2013.01); *A61K 33/30* (2013.01); *A61K 33/32* (2013.01); *A61K 47/00* (2013.01); *A61Q 3/00* (2013.01); *A61Q 5/00* (2013.01); *A61Q 5/02* (2013.01); *A61Q 7/00* (2013.01); *A61Q 19/00* (2013.01); *A61K 9/006* (2013.01); *A61K 9/0034* (2013.01)

(58) Field of Classification Search
CPC ..... A61K 31/194; A61K 1/56; A61K 31/573; A61K 31/60; A61K 33/30; A61K 47/00; A61K 33/32
See application file for complete search history.

(56) References Cited

U.S. PATENT DOCUMENTS

| | | |
|---|---|---|
| 5,639,459 A | 6/1997 | Bouras |
| 5,648,389 A | 7/1997 | Gans et al. |
| 6,407,141 B1 | 6/2002 | Hart |
| 6,936,579 B2 | 8/2005 | Urban |
| 6,982,097 B2 | 1/2006 | Mingzhong et al. |
| 7,517,842 B2 | 4/2009 | Barnhart et al. |
| 7,618,658 B2 | 11/2009 | Tsuchida et al. |
| 7,883,715 B2 | 2/2011 | Abraham et al. |
| 2007/0027119 A1 | 2/2007 | Ahmed et al. |
| 2007/0184016 A1 | 8/2007 | Macinga et al. |
| 2010/0234460 A1 | 9/2010 | Foret et al. |
| 2010/0292333 A1 | 11/2010 | Mladenovich |
| 2011/0152384 A1 | 6/2011 | Gunn et al. |
| 2012/0015809 A1 | 1/2012 | He et al. |
| 2012/0269751 A1 | 10/2012 | Stal |
| 2012/0302642 A1 | 11/2012 | Post |

OTHER PUBLICATIONS

Sigmundsdottir, Trends in Pharmacological Sciences 31 (2010) 239-245.*
R Von Burg, Journal of Applied Toxicology, vol. 14(3),233-237 (1994).*

* cited by examiner

*Primary Examiner* — Savitha Rao
*Assistant Examiner* — Angela Brown-Pettigrew
(74) *Attorney, Agent, or Firm* — Michael E. Zall

(57) ABSTRACT

The present invention is directed to method of treating a patient suffering from hyperhidrosis by administering a composition comprising a low concentration of sodium oxalate, oxalic acid and hydrocortisone.

3 Claims, No Drawings

BROAD SPECTRUM PHARMACOLOGICAL COMPOSITION FOR TREATMENT OF VARIOUS INFECTIONS AND DISEASES AND METHODS OF USE

BACKGROUND OF THE INVENTION

1. Field of the Invention

The present invention relates to a pharmacological composition that is a safe and effective broad spectrum antibiotic, particularly against gram positive and gram negative bacteria, anti-protozoal, and can be used for the treatment of various diseases and for the treatment of various dermatological disorders in patients. In particular, the composition of this invention, inhibits the growth or destroys the bacteria, and inhibits or destroys protozoal infections. The active ingredients in the preferred pharmacological composition are a) a mixture of sodium citrate and citric acid, and/or b) a mixture of sodium oxalate and oxalic acid. However, similar mixtures of the active cation of sodium salts with anions of organic acids may be derived from other organic acids other than citric and oxalic acids, for example, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid and combinations thereof.

2. Related Art

Applicant is aware of the following references that may be relevant to this invention:

US Published Application 2007/0027119 to Ahmed et al. describes a nonirritating antimicrobial liquid composition with citric acid and oxalic acid combination and alcohol used in skin treatment, primarily a teat treatment for cows.

US Published Application 2007/0184016 to Macinga et al. describes a pre-surgical disinfectant with alcohol and citric acid, oxalic acid or mixtures thereof.

US Published Application 2010/0234460 to Foret et al. describes disinfectant solution for the treatment of hoof diseases that contains a surfactant and one or more carboxylic acids, e.g., citric acid and oxalic acid.

US Published Application 2010/0292333 to Mladenovich describes fungal infection treatment composed of two or more low-molecular weight organic acids, e.g., oxalic acid and citric acid, and their salts.

US Published Application 2011/0152384 to Gunn et al. describes skin care composition with emulsifier and organic acids, including oxalic acid or citric acid.

US Published Application 2012/0015809 to He et al. describes a surface cleaner with formic acid and an enhancing component of citric acid that may be mixed with oxalic acid for the control of pests, including fungi, oomycetes, nematodes and weeds.

US Published Application 2012/0269751 to Stal describes a topical composition of physiologically acceptable carboxylic acid such as citric acid and/or oxalic acid for the treatment of skin and nail conditions, i.e., microbiological infections of the nail (onychomycosis), warts.

US Published Application 2012/0302642 to Post abrasive acidic cleaning composition for hard surfaces, e.g., lavatory surfaces, which includes a colloid forming clay, a thickener, a surfactant and antimicrobial amounts of an organic acid and an abrasive constituent. The organic acid may be a citric acid, oxalic acid or mixtures thereof.

U.S. Pat. No. 5,639,459 to Bouras describes a composition to treat hair loss, baldness and alopecia that embodies using oxalates, e.g., ammonium oxalate meta. The use of citric acid is in conjunction therewith is taught. The treatment " . . . enhances the aesthetic appearance of scalp and skin."

U.S. Pat. No. 5,648,389 to Cans et al. describes a topical treatment for dermatological disorders using zinc compound and a hydroxy acid that may be citric acid and the zinc compound may be zinc oxalate.

U.S. Pat. No. 6,936,579 to Urban describes a hard surface cleaning composition with citric acid and oxalic acid.

U.S. Pat. No. 6,982,097 to Mingzhong et al. describes a biocide composition for disinfecting water that includes a filler of sodium citrate, oxalic acid, sodium bromide, and a halogen releasing compound.

U.S. Pat. No. 7,517,842 to Barnhart et al. describes an antimicrobial hand wash formulation with a cationic surfactant produced from the neutralization of an amidoamine with an acid and an active ingredient. The acid may be an oxalic acid or citric acid as the acid neutralizer.

U.S. Pat. No. 7,618,658 to Tsuchida et al. describes an antimicrobial composition of Sasa extract and the use of citric acid or oxalic acid to improve the antimicrobial activity.

U.S. Pat. No. 7,883,715 to Abraham et al. describes enhancing the herbicidal effectiveness of glyphosate through the addition of a dicarboxylic acid, in particular oxalic acid.

U.S. Pat. No. 6,407,141 to Hart describes a hemotherapeuticchemo preventative composition for treating vascular diseases that contains oxalic acid and/or oxalate.

OBJECTS AND SUMMARY OF THE INVENTION

The present invention is directed to a pharmacological composition for the treatment of bacterial and protozoal infections in a patient. The pharmacological composition comprises a pharmaceutical carrier and an active composition selected from the group consisting of an amount of an active cation sodium salt with an anion organic acid and an amount of the organic. The organic acid is selected from the group consisting of citric acid, oxalic acids, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid or combinations thereof. The amounts and weight ratios of such amounts in the active composition result in a safe and effective pharmacological composition.

The preferred pharmacological composition comprises a pharmaceutical carrier and an active composition selected from the group consisting of:

a. an amount of sodium oxalate and an amount of oxalic acid, b. an amount of sodium citrate and an amount of citric acid, or c. mixtures of a. and b, The amounts and weight ratios of a) the sodium oxalate and oxalic acid, and b) the sodium citrate and citric acid in the active composition are such as to produce a safe and effective pharmacological composition.

The invention also relates to the method of using the pharmacological composition for the safe and effective treatment of bacterial infections, protozoal infections and dermatological diseases.

DETAILED DESCRIPTION OF THE INVENTION

Unless specified otherwise, all ingredients are in weight/weight percent (w/w %), i.e., the weight of the ingredient relative to the weight of the final composition described as a percentage.

A "therapeutically effective amount" means the amount of the pharmacological composition described herein that will disinfect, inactivate or significantly diminish the population of a microorganism or protozoa, or effectively treat a given disease or condition, e.g., bacterial infection, protozoal infection, or dermatological diseases or infections.

Preferred Active Composition: Sodium Oxalate and Oxalic Acid

The theoretical stoichiometric ratio of oxalic acid and sodium bicarbonate for the preparation of sodium oxalate is 1:1.33 weight ratio. Theoretically this produces 100% sodium oxalate.

The active composition used in the pharmacological compositions of this invention uses a 1:1 weight ratio of oxalic acid to sodium bicarbonate to make the active composition. This produces a final active composition with an excess of oxalic acid mixed with sodium oxalate. This imparts a safe and efficacious medicinal activity to the composition. The active composition maintains a pH of about 6 which acceptable for patient use.

The highly preferred composition is a mixture of 78.44% sodium oxalate and 21.56% oxalic acid. A preferred range is about 73% to about 83% Sodium oxalate and about 17% to about 27% oxalic acid. It is to be understood however that various weights and ratios of sodium oxalate and oxalic acid may be used as long as a safe and efficacious pharmacological composition is produced.

Sodium Oxalate—Oxalic Acid Mixture
a) Stoichiometric Formulation Ratio:

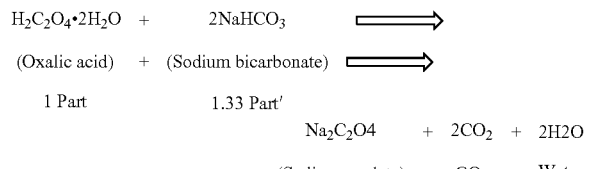

b) Method of Producing Active Composition:

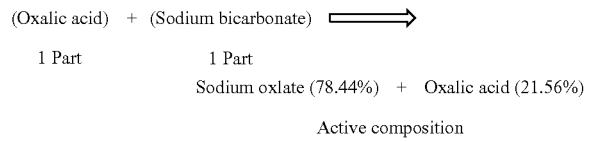

Method of Preparation of Mixture of Sodium Oxalate—Oxalic Acid as Active Ingredient Mix one part oxalic acid and one part sodium bicarbonate than gradually spray sterile water into the mixture to make reaction. The water is merely the medium for the reaction. Carbon dioxide is evaporated rapidly and water is gradually evaporated. The remaining product is a mixture of 78.44% Sodium Oxalate and 21.56% Oxalic acid active ingredient. The product is in the form of crystals. The product is then dried and crushed to fine particles to produce an active composition suitable for formulation into the pharmacological formulations of this invention.

Preferred Active Composition: Sodium Citrate and Citric Acid

The theoretical stoichiometric ratio of citric acid and sodium bicarbonate for the preparation of sodium oxalate is 1:1.2 weight ratios. Theoretically this produces 100% sodium citrate. The active composition used in the pharmacological compositions of this invention uses a 1:1 weight ratio of citric acid to sodium bicarbonate to make the active composition. This produces a final active composition with an excess of citric acid mixed with sodium citrate. This imparts a safe and efficacious medicinal activity to the composition. The active composition maintains a pH of about 6 which acceptable for patient use.

The highly preferred composition is a mixture of 87% sodium citrate and 13% citric acid. A preferred range is about 82% to about 92% Sodium citrate and about 8% to about 18% citric acid. It is to be understood however that various weights and ratios of sodium citrate and citric acid may be used as long as a safe and efficacious pharmacological composition is produced.

Sodium Citrate—Citric Acid Mixture
a) Stoichiometric Formulation Ratio:

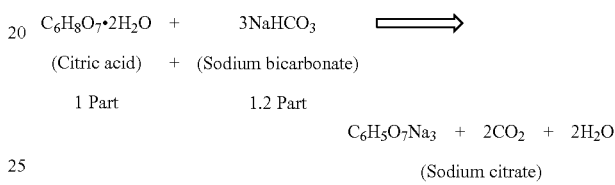

b) Method of Producing Active Composition:

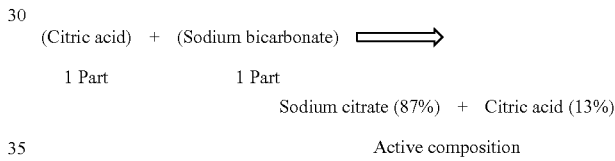

Method of Preparation of Mixture of Sodium Citrate—Citric Acid as Active Ingredient Mix one part citric acid and one part sodium bicarbonate than gradually spray sterile water into the mixture to make reaction. The water is merely the medium for the reaction. Carbon dioxide is evaporated rapidly and water is gradually evaporated. The remaining product is a mixture of 87% Sodium citrate and 13% citric acid active ingredient. The product is in the form of crystals. The product is then dried and crushed to fine particles to produce an active composition suitable for formulation into the pharmacological formulations of this invention.

Similar mixtures of sodium salts and organic acids may be derived from other organic acids other than citric and oxalic acids, for example, lactic acid, salicylic acid, tartaric acid, glycolic acid, ascorbic acid, maleic acid, succinic acid, mandelic acid, dodecylbenzenesulfonic acid, propionic acid, gluconic acid, malic acid, benzoic acid, aspartic acid, acetic acid, glutamic acid, adipic acid, hexanoic acid, octanoic acid, nonanoic acid, decanoic acid, undecanoic acid and combinations thereof.

The pharmacological compositions of this invention include a pharmaceutically acceptable carrier that does not adversely affect the efficacy and safety of the compositions. The carrier is highly dependent on the selected modality of treatment. For example, the pharmacological compositions may be orally administered, topically applied, administered as a suppository, and as an injectable. The carrier may include, for example, an additive selected from a buffering agent, an emollient, a humectant, a preservative, a surfactant or wetting agent, a viscosity control agent, a colorant, an opacifying agent, and any combinations thereof.

The pharmacological composition may also include additional suitable components, for instance fragrances, emulsifiers, detergents, antioxidants and preservatives, and other ingredients commonly used in pharmaceutical and cosmetic formulations. Preferably, the composition is essentially free of water, which increases the stability of the composition over time. Preferably, the composition is formulated as a fluid composition such as a cream, or more preferably as a liquid composition, which is relatively easy to apply to the human skin and/or nails.

Methods of preparing the pharmacological compositions may involve dissolving a desired concentration of the active composition and, alternatively, any desired additives in a selected pharmaceutical carrier. The solution is then mixed, for example in a mixer, to form a final pharmacological composition. Useful concentrations are those where the percentage of the active composition by total weight of the composition is preferably from about 0.02 to 20% by weight of the pharmacological composition. The pharmaceutical carrier may be present form 80 to 99.98% by weight. More preferably, this is from about 0.03 to 15% of each active composition and from about 85 to 99.97% of a pharmaceutical carrier.

The phrase "therapeutically effective amount" is intended to qualify the amount of the pharmacological composition which will achieve the goal of the composition, e.g., reduction of bacteria, reduction of protozoal activity, and treatment of dermatological diseases. "Therapeutically effective" may also refer to improvement in disorder severity or the frequency of incidence over no treatment.

The term "topical" and "locally" application shall refer to any composition applied on skin, eye, auditory canal, oral mucosa and in vaginal mucosa where the application of my invention is indicated.

Broadly, the pharmacological composition of this invention is used for the treatment of bacterial and protozoal infections in a patient and treating a dermatological disease in a patient.

The pharmacological compositions of this invention may also contain water and a "structuring agent" such as carbomers or other thickening polymers, for example, xanthan gum, carrageenan gum or the like. The compositions may be made into a wide variety of product types that include but are not limited to lotions, sprays, wipes, and make-up such as foundations. These product types may comprise several types of cosmetically-acceptable topical carriers. Preferably the carrier is alcohol free.

Preferred carriers for the active composition, based on the foregoing criteria for use, are:

Preferred Carrier Compositions (by Weight):
1) 20% emulsifying wax, 10% Liquid paraffin and 70% water.
2) 20% emulsifying wax and 80% water.
3) 2% carboxymethyl cellulose and 98% water.

Antibiotic

More specifically the pharmacological compositions are used as a broad spectrum antibiotic. Preferably, the mixture of sodium oxalate and oxalic acid is used alone as the active composition, as is the mixture of sodium citrate and citric acid. A mixture of these active compositions may also be used.

The pharmacological composition of this invention may be used orally, topically in the form of ointment, cream, and drops (for eye and ear). through suppository and parenterally by injection, infusion or implantation. The pharmacological compositions of this invention are effective against gram positive and gram negative bacteria, for example: *Staphylococcus aureus, Epidermidis, Streptococcus Aagalactae, E. coli, Klebsilla, Proteus, Entrobacter, Entrococcous, Citrobacter, Propionibacterium acne, Corynebacterium, B. Subtilis,* and *Serratia* but not limited to these.

The pharmacological composition of this invention may be used where antibiotics are indicated in the treatment of infections caused by pathogens sensitive to it, for example in pneumonia, chronic bronchitis, acute exacerbation of chronic bronchitis, community acquired pneumonia, sinusitis otitis media, urinary tract infection, genital tract gonococci urethritis, non gonococci urethritis, cervicitis, skin and soft tissue infections, chalazion, conjunctivitis, otitis externa, otitis media tympanits, perotinitis, cholecystis, appendicitis, folliculitis, paronychia, carbuncle and other such infections.

Protozoa

The pharmacological compositions of this invention may be used for reducing protozoa in a patient having a protozoalinfection, i.e., an anti-protozoal composition. The composition acts against trichomonads which causes trichomoniasis. It also acts against antamoeba histolytica, causes amaebiasis and Giardia, causes Giardiasis the gastroenteritis intestinalis. Some other protozoa are human parasites, causing diseases. Examples of diseases caused by protozoa, which the compositions of this invention are effective against, are Malaria, Amoebiasis, Giardiasis, Toxoplasmosis, Cryptosporidiosis, Trichomoniasis, Chagas disease, Leishmaniasis, Sleeping Sickness, and Dysentery.

Dermatological Diseases

The pharmacological compositions of this invention may be used for treating dermatological diseases in a patient having such a disease. Preferably, the mixture of sodium oxalate and oxalic acid is used alone as the active composition, as may the mixture of sodium citrate and citric acid. A preferred dermatological pharmacological composition of this invention for the treatment of skin diseases includes about 1% to about 10% of the sodium oxalate and oxalic acid mixture as the active composition or about 1% to about 10% of the sodium citrate and citric acid as the active composition. Optionally, about 1% to about 4% Salicylic acid, steroid (colobetasol, hydrocortisone), Benzoic acid and zinc oxide may be added to enhance the effect of composition. For dry skin, an oily base may be used. For an oily skin, a water base may be used. If the pharmacological composition needs to be taken orally, a nontoxic (edible) water based carrier should be used. If the pharmacological composition is for vaginal use a water or oil base carrier should be used.

Hyperhidrosis

The pharmacological compositions of this invention may also be used for treating hyperhidrosis. Hyperhidrosis is a disease of excessive production of sweat, particularly from the palms, soles and axillae. Hyperhidrosis may be due to pharmacologically acting agents acting on the sweat glands, abnormal stimulation of the sympathetic path-ways between the hypothalamus and nerve endings or over activity of one of three different centers responsible for thermoregulatory, mental and gustatory centers or of unknown cases.

Whatever the underlying cause of hyperhidrosis, the pharmacological compositions of this invention act locally to suppress and/or cure hyperhidrosis by developing anhidrotic areas by directly acting on the sweat glands (eccrine and apocrine glands).

The preferred treatment is with a topical pharmacological composition having 2% to 10% (by weight) of a mixture of sodium citrate and citric acid or, alternatively with a 2% to 10% mixture of sodium oxalate and oxalic acid.

Lice

The pharmacological compositions of this invention may also be used for treating lice. This is accomplished by the direct interference by the compositions of this invention with the respiratory function of the lice by blocking the spiracles of the lice. This is accomplished without any adverse effect on the skin, and particularly to children that would use the composition.

Lice are members of phthiraptera. They spend their entire life on the host, e.g., animals or people. Man is parasitized by two species. Two species are from the sub-order anoplura, and are the *Pediculushumanus* and *pithrus pubis* species. There are two species of *pediculus humanus*, they are *P humanus capitis* (head lice) and *P humanus humanus* (body or clothing lice). *Pithirus pubis* (pubic or crab lice) is morphologically quite distinct from *Pediculus humanus*. Infection with pubic lice is termed pithiriasis while infection with *Pediculus humanus* is termed Pediculosis.

The pharmacological compositions of this invention produce a multi action affect to eradicate the lice. It is pediculicider and ovicider. Eggs of head lice, and empty egg cases are cemented to hair shaft with a chitinous cement material secreted by the female accessory glands and are difficult to dislodge. The compositions of this invention dissolve chitinous material to loosen the eggs so that they can be removed by combing the hair. The pharmacological compositions also have antihydrotic effect and create anhidrotic area in scalp which creates an unfavorable environment for lice development. The compositions when applied locally will kill the lice within 24 hours.

The preferred treatment is with topical pharmacological compositions of a 2% to 10% (by weight) of a mixture of sodium citrate and citric acid or, alternatively with a 2% to 10% mixture of sodium oxalate and oxalic acid.

Scabies

The pharmacological compositions of this invention may also be used for treating Scabies. This is a disease found in man and animal. It is caused by *sarcoptes scabie* and *notoedres cati*. Scabies are caused by mites of Arachnida class *sarcoptes scabiei*.

The mite shows a preference for certain sites in which to burrow and appear to avoid areas with a high density of pilosebeceous follicle. The number of adult female mites in individual suffering from the common form of scabies is about twelve. Only in crusted scabies there are a large number of mites present.

Scabies is usually transmitted by close physical contact such as prolonged hand holding, bed sharing. Poor hygienic condition, encourage the spread of scabies. Scabies is usually found in developing countries and regions of poverty.

The pharmacological compositions of this invention when locally applied are scabicider and functions to minimize secretions from the sebaceous glands. Secretions from the sebaceous glands provide a suitable environment for the growth of mites in humans as well as in animals. The compositions provide a "double action" for the treatment of this disease.

The preferred treatment is with topical pharmacological compositions of a 2% to 10% (by weight) of a mixture of sodium citrate and citric acid or, alternatively with a 2% to 10% mixture of sodium oxalate and oxalic acid. Oral treatment for scabies may also be given for short period of time orally which also work as scabicider.

Fish Malodor

The pharmacological compositions of this invention may also be used for treating Fish malodor caused by sweating, vaginal discharge and/or from mouth and nares. Trimethylaminuria (TMAU), also known as fish odor syndrome or fish malodor syndrome, is a rare metabolic disorder that causes a defect in the normal production of the enzyme flavin containing monooxygenase ("FM03"). When FMO3 is not working correctly or if not enough enzyme is produced, the body loses the ability to properly convert trimethylamine (TMA) from precursor compounds in food digestion into trimethylamine oxide (TMAO) through a process called N-oxygenation. Trimethylamine then builds up and is released in the person's sweat, urine, and breath, giving off a strong fishy odor or strong body odor. Other names: Mal fish odor smell from sweating, Bromhidrosis and fish odor syndrome and osmidrosis.

Odor of skin in men to a large extend determined by apocrine glands secretion. Sebeceous glands secretions have some odor also. Decomposition of keratinization especially in the presence of hyperhidrosis produces offensive smell. Eccrine gland secretion is odorless but various substances may be excreted in it for example garlic.

Characteristic odors may be associated with various uncommon amino-acidurias; trimethyl-aminuria gives rise to the fish odor syndrome. This odor is unpleasant and people avoid sitting near such persons.

The pharmacological compositions of this invention acts as a deodorant by rendering the the application area anhidrotic. As it suppresses the sweat secretion of both apocrine and eccrine sweat gland it also suppresses sebecous gland secretion sebum. It also prevents bacterial activity which decomposes and liberates fatty acids with its characteristic smell. The pharmacological compositions of this invention were used by 30 patients and the composition was efficacious.

The preferred treatment is with topical pharmacological compositions of a 2% to 10% (by weight) of a mixture of sodium citrate and citric acid or, alternatively with a 2% to 10% mixture of sodium oxalate and oxalic acid.

Vaginal Mal Fish Odor

The pharmacological compositions of this invention may also be used for treating vaginal mal fish odor. This is the commonest form of vaginitis. The patient complains of an excessive grey, thin discharge associated with a fishy odor. This disorder is associated with infection by aerobic Gram negative rod known as *gardnerella* vaginitis. This organism alone is incapable of causing infection and now specific vaginitis is now regarded as complex interrelationship between *gardnerella* and anaerobic species of bacteria of which genus *mobiluncus* have been identified only and their over growth within the vagina give increase in secretion and fishy mal odor.

The preferred treatment is with topical pharmacological compositions of a 2% to 5% (by weight) of a mixture of sodium citrate and citric acid or, alternatively with a 2% to 10% mixture of sodium oxalate and oxalic acid.

Mal Fish Odor from Mouth

Mal fish odor from mouth and nose is a bad and unpleasant smell from the mouth and nose.

The preferred treatment is with a topical pharmacological composition of a 2% to 10% (by weight) of a mixture of sodium citrate and citric acid or, alternatively with a 2% to 10% mixture of sodium oxalate and oxalic acid.

Morphoea

The pharmacological compositions of this invention may also be used for treating Morphoea (Sclerosis of skin). Morphea is a medical term for localized *scleroderma*. The disease involves isolated patches of hardened skin—there generally is no internal organ involvement. The condition may be subdivided clinically into many types. In this disease skin become thickened, elastic tissue is reduced and the skin becomes hard. The surface is usually smooth and the wrinkles in the skin are lost. Facial expressions may also be lost.

The pharmacological compositions of this invention when topically applied cause resolution of such cases with excellent results.

The preferred treatment is with topical pharmacological compositions of a 2% to 10% (by weight) of a mixture of sodium citrate and citric acid or, alternatively with a 2% to 10% mixture of sodium oxalate and oxalic acid. From 1% to 2% salicylic acid and/or 0.025% to 0.05% clobetasol propionate may be added to the pharmacological composition.

Hypermelanosis

The pharmacological compositions of this invention may also be used for treating Hypermelanosis, a condition where there is excessive melanin deposition in the skin or in the oral mucous. This may be congenital or acquired through a drug reaction, melasma, addisions diseases, dyskeratosis congenital, post inflammatory hypermelanosis, berloque dermatitis, hypermelasnosis due to naevus of ITO, blue naevus, photodynamic and phototoxic reaction, hepatic cirrhosis (cause diffuse pigmentation), amyloidosis, pellagra, Mongolian spots and etc.

The pharmacological compositions of this invention when locally applied cures, diminishes or decreases such hypermelanotic pigmented spots.

The preferred treatment is with topical pharmacological compositions of a 2% to 10% (by weight) of a mixture of sodium citrate and citric acid or, alternatively with a 2% to 10% mixture of sodium oxalate and oxalic acid. Additionally, 0.025% to 0.05% clobetasol propionate and 2% to 3% salicylic acid may be added to the pharmacological composition.

Deformed Nails

The pharmacological compositions of this invention may also be used for treating Deformed Nails. Such nails are either congenitally or acquired through activity and environment. Without limiting the scope of the invention, there are several type nail deformities:

1. Habit deformity—the deformity consists of a depression down the center of one nail.
2. Splitting into layers—the tips of the nails split into layers and pieces may flake.
3. Onychogryphosis—the nail become curved like a ram's horn.
4. Beau's lines—a transverse depression in nails.
5. Regular pitting-Excess ridging with or without pitting.

The preferred treatment is with topical pharmacological compositions of a 2% to 10% (by weight) of a mixture of sodium citrate and citric acid or, alternatively with a 2% to 10% mixture of sodium oxalate and oxalic acid.

Nail Growth

The pharmacological compositions of this invention may be used to enhance the growth of nails which are broken before attaining its normal length.

The preferred treatment is with topical pharmacological compositions of a 2% to 10% (by weight) of a mixture of sodium citrate and citric acid or, alternatively with a 2% to 10% mixture of sodium oxalate and oxalic acid.

Hair Fall and Alopecia

The pharmacological compositions of this invention may also be used for effectively treating Hair Fall and Alopecia.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally, 1.5% salicylic acid, 3% benzoic acid and 0.025% clobetasol propionate may be added.

Rosacea.

The pharmacological compositions of this invention may also be used for treating Rosacea. Rosecea is a chronic skin disorder, usually affecting the convexities of the face and characterized by redness of the skin, telengiectasia and episodes of inflammation. During an attack of inflammation the effected skin typically develops papules, pustules and swelling. The disease is common at ages 30-50 years old. The disease is also prominent in women.

Cardinal physical signs include 1) Erythema 2) Talengiectasia 3) Papules 4) Swelling 5) Pustules. The pharmacological compositions of this invention when therapeutically and locally applied reduce inflammation, anti-erythematic and keratolytic activity and reduce the number of episodes.

The preferred treatment is with topical pharmacological compositions of a 1% to 5% (by weight) of a mixture of sodium citrate and citric acid or, alternatively with a 1% to 5% mixture of sodium oxalate and oxalic acid. Additionally, optionally 5% to 10% zinc oxide may be added as sun screening agent and also as to prevent irritation to the composition.

Acne

The pharmacological compositions of this invention may also be used for treating acne. All types of acne may be treated.

Acne is chronic inflammatory disease affecting more than 80% of adolescents and may continue through adulthood. Some individuals suffer from acne into the thirties and even beyond. Lesion acne is most frequently found on face, neck and back, chest, shoulders and upper arms. Acne is characterized by the formation of comedones, papules, pustules, less frequently nodules or syst and in some cases scarring. A peak of incidents is usually between 14 to 19 years. Four major factors in its pathogenesis Increased Sebum Production
1) Keratinization of pilosebeceous duct
2) Abnormality of microbial flora
3) Production of inflammation
4) Hydration The pharmacological composition of this invention when therapeutically locally applied inhibits sebum secretion and also inhibits sweat gland secretion and provides an anhidrotic skin area. The pharmacological compositions of this invention also have mild karatolytic activity and diminish keratinization. The antibiotic properties provide a sterile surface preventing or minimizing causative bacteria p-acne, as well as microbial flora. The composition also acts as an anti-inflammatory.

The preferred treatment is with a topical pharmacological composition of a 1% to 5% (by weight) of a mixture of sodium citrate and citric acid or, alternatively with a 1% to 5% mixture of sodium oxalate and oxalic acid. Optionally, 1% to 2% salicylic acid may be added. In severe conditions 0.5% to 1% hydrocortisone may be added for a short period of time. A widely used treatment for cystic acne is direct local injection into the cyst, which is very painful and may cause leocoderma on the skin, i.e., the skin becomes depigmented. With the treatment described herein, the cystic acne is treated with 2% to 5% of the pharmacological composition along with 0.025% to 0.05% Clobetasol propionate in suitable oil free cream applied locally. Such a treatment provides excellent results to dissolve cyst.

*Pityriasis Rosea*

The pharmacological compositions of this invention may also be used for treating *Pityriasis Rosea*. *Pityriasis rosea* is an acute and self-limiting disease. The exact cause of the skin condition is unknown, probably infective in origin, affecting mainly children and young adults and characterized by distinctive skin eruption and minimal constitutional symptoms. *Pityriasis Rosea* eruption has been associated with drugs such as arsenic, bismith, gold, captopril, ketototifen, etc. The eruption of *pityriasis Rosea* follows a distinctive and remarkably constant pattern. Lesions are defined bright red, round or oval plaque, soon covered by fine scales. Lesions erupt in crops.

The pharmacological compositions of this invention when topically applied locally, the skin lesions subside within five to fifteen days. It is theorized that the mechanism of its action is keratolytic and anti-bacterial.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally, 1% to 2% salicylic acid may be added.

Psoriasis

The pharmacological compositions of this invention may also be used for treating Psoriasis. Psoriasis is a genetically determined inflammatory and proliferative disease of skin, most characteristic lesions consisting of chronic, sharply demarcated, dull red scaly plaques. Provocative factors involved trauma, infection, sun light, metabolic factor drugs and etc.

The preferred treatment is with a topical pharmacological composition of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Lichen Planus

The pharmacological compositions of this invention may also be used for treating Lichen planus. Lichen planus is an immunologically mediated disease. Commonly presented as a skin lesion that is shiny, polygonal and violates papules. The lesion varies in size from a pin point to a centimeter or more and may be closely aggregated or widely dispersed. On the surface there may be Wickham's striae. Buccal mucosa and the tongue are most often involved but the anus and genitalia may also be involved. Lichenoid drug eruptions may occur due to certain drugs, for example, mepacrine, isoniazid.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added. An oral composition may also be used for treatment.

Seborrhoeic Dermatitis

The pharmacological compositions of this invention may also be used for treating Seborrhoeic Dermatitis. It is a chronic dermatitis characterized by distinctive morphology including red sharply marginated lesions covered with greasy looking scales and a distinctive distribution in areas with a rich supply sebaceous glands namely the scalp, face and upper trunk. Dandruff appears to be the precursor of seborrhoeic dermatitis. The yeast *malassezia furfur* is increased in seborrhoeic dermatitis. *P. ovale* is also found.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Tinea

The pharmacological compositions of this invention may also be used for treating *Tinea* (Fungal Infections). The present compositions are suitable as broad spectrum, topical antifungal preparations for the treatment of a variety of fungal infections that may develop on the skin and nails, or which may be present and viable on surfaces which may come in contact with skin and nails. As a result, the compositions of the present invention may be used either therapeutically to treat a pre-existing infection, or as a fungicidal disinfectant to cleanse surfaces that may harbor the fungus, thereby preventing or limiting the occurrence of infections. The compositions are used to topically treat fungal infections that may develop on the skin (dermatomycoses) as well as toe and finger nails (onychomycosis). These fungal infections, also commonly known as *Tinea pedis* (athlete's foot), *Tinea unguium* (nail infections), *Tinea cruris, Tinea corporis, Tinea versicolor* and *candidiasis*, among others, are caused by different types of fungus such as those of the gena *Trichophyton, Epidermophyfon, Microsporum* and *Candida*.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 1% to 2% salicylic acid, 5% to 10% zinc oxide may be added. An oral composition may also be used for treatment.

Oral Submucous Fibrosis

The pharmacological compositions of this invention may also be used for treating Oral Sub mucous Fibrosis. This disease can follow burns, irradiation but commonly and particularly this disease occurs due to habit of chewing of betelnut which predisposed to oral sub mucus fibrosis. In such condition there is loss of elasticity of oral tissues. This disease is particularly found in Indian sub-continent. Pathologically there is fibrosis extending to sub mucosa and muscles. Epithelial changes included atrophy to keratosis. This disease, when severe, restricts the mouth from opening. The patient is unable to eat and even talk properly. This disease may transform into squamous cell carcinoma. Management of this disease is very difficult. Only intralesional corticosteroids injection locally has been found to help, otherwise surgery is needed. The pharmacological compositions of this invention when applied locally in a cream or in a jelly form have excellent (almost 100%) beneficial effect, resulting in the patient being able to reopen his/her of mouth to a large extent. Twenty-five (25) patients who were habitual chewers of the betel nut were the patients.

The preferred treatment is with a topical pharmacological compositions of a 2% to 10% (by weight) of a mixture of sodium citrate and citric acid or, alternatively with a 2% to 10% mixture of sodium oxalate and oxalic acid.

Amyloidosis

The pharmacological compositions of this invention may also be used for treating Amyloidosis. Amyloidosis is a disease in which there is a deposition of a proteinous substances composed of one of family of biochemically unrelated proteins which is associated with considerable dysfunction. Amyloid deposits also contain extra cellular matrix component including glycosaminoglycans and proteoglycans which may be involved in pathogenesis.

The pharmacological compositions of this invention were tested on papular (lichen) amyloidosis and upon macular amyloidosis in 24 patients and found to be effective.

Amyloidosis is classified as follows:
1) Primarily localized cutaneous Amyloidosis
2) Secondarily localized cutaneous Amyloidosis
3) Systemic Amyloidosis The pharmacological compositions of this invention are used to therapeutically treat skin (cutaneous) amyloidosis whatever the cause. My invention only treats and treated with success all skin conditions, where there is deposition of amyloid.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Purpura

The pharmacological compositions of this invention may also be used for treating Purpura. Purpura is discoloration of skin or mucous membranes due to extra extravasations of red blood cells due to many causes. The skin becomes purpuric. Purpura may be caused by raised intravascular pressure. There are several types, e.g., senile purpura, corticosteroid purpura, drug purpura, contact purpura, schamberg purpura, coagulation defects purpura and etc.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally, 0.025% to 0.05 clobetasol propionate may be added to the pharmacological composition.

Discoid Lupus Erythematosus.

The pharmacological compositions of this invention may also be used for treating Discoid lupus erythematosus. This disease is an autoimmune disease characterized by eruption of scaly patches atrophy, scarring and pigmentary changes, and most frequently involving the face. The disease affects twice as many females as males.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid and/or 0.025% to 0.05% clobetasol propionate may be added.

Contact Dermatitis

The pharmacological compositions of this invention may also be used for treating Contact dermatitis. Any antigen that comes in contact with skin may react with the skin causing contact dermatitis. It may be either primary irritant contact dermatitis or primary allergic contact dermatitis. For example, there is shoe dermatitis, hair dye contact dermatitis, nickel dermatitis, washing powder dermatitis, etc. The skin becomes scaly, pigmented and itchy and in some cases oozing.

The preferred treatment is with topical pharmacological compositions of a 1% to 10% (by weight) of a mixture of sodium citrate and citric acid or, alternatively with a 1% to 10% mixture of sodium oxalate and oxalic acid. Optionally 2% to 4% salicylic acid and/or 0.025% to 0.05% clobetasol propionate and 5% to 10% zinc oxide may be added as for sun screening agent and also for as soothing effect.

Hair and Skin Shiner

The pharmacological compositions of this invention may also be used as a hair and skin shiner. The compositions make the hair and skin shine, reflect the light causing an attractive look. This invention may be incorporated in shampoo and in face cream.

The preferred treatment is with topical pharmacological compositions of a 2% to 10% (by weight) of a mixture of sodium citrate and citric acid or, alternatively with a 2% to 10% mixture of sodium oxalate and oxalic acid.

Mollascum Contagious.

The pharmacological compositions of this invention may also be used for treating Mollascum contagious. This is viral infection of skin caused by an unclassified member of poxviridae in mollascum contagiousam lesion, characterized by papules and nodules. Its general treatment included cryotherapy, squeezing its forceps (a painful procedure), application of silver nitrate or phenol with stick and etc.

The preferred treatment is with topical pharmacological compositions of a 2% to 10% (by weight) of a mixture of sodium citrate and citric acid or, alternatively with a 2% to 10% mixture of sodium oxalate and oxalic acid. Optionally 2% to 4% salicylic acid may be added.

Herpes Simplex

The pharmacological compositions of this invention may also be used for treating Herpes simplex. This is viral infection is caused by herpes virus hominis (herpes simplex virus, HSV). It is a common infection in men. Skin shows vesicles presenting as white plaques are present. Skin, tongue, buccal mucous membrane, palate, genital area and etc. are involved.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 1% to 2% salicylic acid and 5% to 10% zinc oxide may be added.

Paronychia

The pharmacological compositions of this invention may also be used for treating Paronychia. Paronychia is a painful full swelling of nail folds. It commonly occurs in persons whose hands are excessively exposed to water. It may result from local injuries for example nail biting, splits or there may be no preceding injuries. It is a common complaint and is usually due to bacterial infection including staphylococcal, other organisms involved in it may be *streptococci, pseudomonas, proteus vulgars* and it may also be due to other causes for example fungal infection, *candida albicans* infection, etc.

The preferred treatment is with topical pharmacological compositions of a 2% to 5% (by weight) of a mixture of sodium citrate and citric acid or, alternatively with a 2% to 5% mixture of sodium oxalate and oxalic acid. Optionally 2% to 4% salicylic acid may be added.

The active compositions of this invention are rapidly and highly soluble in water and thus are rapidly absorbed onto and into wet skin rather than on dry skin. It is thus preferred that the compositions be topically applied to skin that has been moistened with water.

As the active composition when applied to the skin can create dryness, it is thus desirable to have a formulated pharmacological composition that is greasy. However, when treating acne this drying ability is beneficial and thus the final composition should be non-greasy or have less of a greasy feel or property.

The active compositions are rapidly absorbed percutaneously and enter in to the bloodstream. Therefore it is advisable that when the drug is applied to a large area, for example in the treatment of psoriasis, the patient should be kept under observation by the physician.

The active composition may also lower blood pressure as it is absorbed through the skin. It is thus advisable not to treat patients less than 5 years old or applied under strict supervision at a low concentration of active composition and/or treating small areas.

If given orally it may cause nausea, vomiting and diarrhea. It therefore should be taken a half hour before food or one hour after food.

While various changes may be made in the detailed construction and processes of this invention, it will be understood that such changes will be within the spirit and scope of the present invention. Having thus described the invention in detail, it is to be understood that the foregoing description is not intended to limit the spirit and scope thereof. What is desired to be protected by Letters Patent is set forth in the appended claims.

What is claimed:

1. A method of treating a dermatological disease of hyperhidrosis in a patient having such disease, comprising topically applying more than two times per day a therapeutically effective amount of a pharmacological composition comprising:
   a pharmaceutical carrier;
   an active composition consisting of an amount of about 73% to about 83% sodium oxalate and about 17% to about 27% oxalic acid, and
   hydrocortisone,
   wherein the active composition is present at from about 0.02 to 20% of the pharmacological composition, and the hydrocortisone is present at about 1% to 4% of the pharmacological composition,
   wherein the pharmacological composition is safe and effective for the treatment of the dermatological disease of hyperhidrosis.

2. The method of claim 1, wherein the active composition consists of about 78.5% Sodium oxalate and about 21.5% oxalic acid.

3. The method of claim 1, wherein the active composition is present at from about 0.03 to 15% of the pharmacological composition.

* * * * *